United States Patent [19]
Grant

[11] Patent Number: 5,682,905
[45] Date of Patent: Nov. 4, 1997

[54] INTRAVENOUS INJECTION SHIELD ASSEMBLY

[76] Inventor: Michael L. Grant, 6000 Greenview Dr., Oklahoma City, Okla. 73135

[21] Appl. No.: 695,816

[22] Filed: Aug. 5, 1996

[51] Int. Cl.⁶ ............................................. A61F 5/37
[52] U.S. Cl. ............................... 128/877; 128/878; 128/879; 128/888
[58] Field of Search ............................ 128/846, 877, 128/878, 888, 882, 879; 602/5, 21, 22

[56] References Cited

U.S. PATENT DOCUMENTS

| | | | |
|---|---|---|---|
| 3,256,880 | 6/1966 | Caypinar | 128/877 |
| 4,870,976 | 10/1989 | Denny | 128/877 |
| 4,919,150 | 4/1990 | Grant | 128/877 |
| 5,018,534 | 5/1991 | Grant | 128/877 |
| 5,339,834 | 8/1994 | Marcelli | 128/877 |
| 5,413,120 | 5/1995 | Grant | 128/877 |

*Primary Examiner*—Michael A. Brown
*Attorney, Agent, or Firm*—Robert K. Rhea

[57] ABSTRACT

An intravenous catheter shield is formed by a base having side walls underlying a portion of a hand and forearm of a patient having an inserted infusion needle. The side walls at one side of the base define a thumb nesting recess therebetween. Resilient padding is interposed between the base and the patient's hand and forearm and straps extending transversely across the patient's hand releaseably secure it to the base. An inverted transparent generally U-shaped shield has leg portions removably secured to the base side walls with the bight portion of the shield in vertically spaced relation, with respect to the patient's hand, permitting visual inspection of a venipuncture site at all times.

1 Claim, 2 Drawing Sheets

INTRAVENOUS INJECTION SHIELD ASSEMBLY

BACKGROUND OF THE INVENTION

1. Field of the Invention

This invention relates to medical equipment and more particularly to a guard or shield for a venipuncture site.

When fluid is be to be intravenously injected into a patient, it has been the general practice to insert a cannula beneath the surface of the skin into a vein and retain the cannula in position by adhesive tape. This simple arrangement is effective; however, problems may arise in that the adhesive tape sometimes prevents visual inspection of the venipuncture site and often provides inadequate retention of the cannula as the patient moves or as the nurse inserts a needle to inject other medications.

Further, children who may be quite active are not capable of or at least do not protect the venipuncture site and may dislodge the cannula in their activity.

Additionally, the adhesive tape may be irritating if a patient's skin is sensitive to the tape creating discomfort for the patient in the area of the venipuncture site.

This invention provides a lightweight rigid device which substantially immobilizes a patient's hand and provides a transparent shield for visual inspection of a venipuncture site while retained on the patient's hand.

2. Description of the Prior Art

The most pertinent patent is believed to be my U.S. Pat. No. 5,413,120 issued May 9, 1995 for INTRAVENOUS INJECTION SHIELD ASSEMBLY. This patent discloses a rigid base underlying a hand and forearm portion of a patient having an inserted infusion needle. The base is provided with opposing upstanding longitudinally spaced side walls having a recess intermediate the base ends for receiving the thumb of a patient's hand overlying the base and secured thereto by transversely extending straps. An inverted generally U-shaped shield has forward and rearward legs portions removably secured to the inner surface of the base side walls with the bight portion of the shield in vertically spaced relation with respect to the patient's hand and apertured for the passage of tubing extending from a cannula venipuncture site.

Examples of the state-of-the-art are believed shown by my U.S. Pat. Nos. 4,919,150 issued Apr. 4, 1990 and 5,018,534 issued May 28, 1991 both for INTRAVENOUS CATHETER SHIELD AND RETAINER. These patents disclose a planar base underlying a patient's hand and forearm and secured thereto by overlapping VELCRO straps extending transversely of the base. U.S. Pat. No. 4,919,150 discloses a lift off transparent shield covering the patient's hand and forearm and supporting a catheter tube. U.S. Pat. No. 5,108,534 similarly discloses a transparent shield overlying the base of a patient's hand and forearm and is hingidly connected thereto for permitting access to the catheter.

This invention is believed distinctive over these patents by providing a rigid relatively lightweight base having integral forward and rearward upstanding side walls at one side of the base and an opposite upstanding side wall medially the ends of the other side of the base overlaid by soft padding having a nap cooperatively gripping a section of VELCRO when impressed thereon. The VELCRO equipped straps extend transversely of the base underside and over the patient's hand and fingers for attaching the base to the patient's hand.

A generally U-shaped when installed overlying plastic transparent shield is separably secured by its legs to the base side walls.

SUMMARY OF THE INVENTION

A rectangular rigid base dimensioned to underlie the palm portion of a patient's hand, excluding the thumb, is provided with an overlying pad or cushion and forward and rearward hollow walls forming a thumb receiving position therebetween. Each of the forward and rearward hollow walls have a slot top opening and project upwardly a distance not greater than one-half the width of the base member. The opposite side of the base is provided with a hollow wall medially its ends of equal height with respect to the forward and rearward walls. The base and at least the inner surface of the walls are overlaid with fabric material having a soft nap cooperatively gripping a section of VELCRO when applied thereto.

One side of the base is apertured adjacent its respective ends for receiving one end portion of a hook and eye VELCRO strap projecting therethrough for overlying and securing the patient's wrist and fingers to the base in a wrap around action of the hand and base.

An inverted transversely U-shaped shield formed from transparent flexible plastic material having a memory returning its leg like walls to a planar position after being flexed toward base connected U-shape is provided with a VELCRO pad at the depending end portion of one of its legs for contacting the inner surface of the undivided base side wall. The opposite U-shaped leg is recessed medially its side edges to define a pair of leg strips removably received by the slot openings in the forward and rearward hollow side walls. The leg strips are provided, on one vertical side edge, with a notch engaging an end wall surface of the respective opening in the hollow walls to prevent accidental removable of the shield straps from the double wall opening and permit an operator to easily remove the opposite side of the inverted U-shaped shield for accessing the intravenous catheter or puncture site.

The principal object of this invention is to provide a relatively light weight intravenous needle shield which immobilizes a patient's hand and fingers with respect to an underlying padded base and permits visual inspection of a catheter site at all times and ease in removing the transparent shield when desired.

DESCRIPTION OF THE PREFERRED EMBODIMENTS

Figure 1:
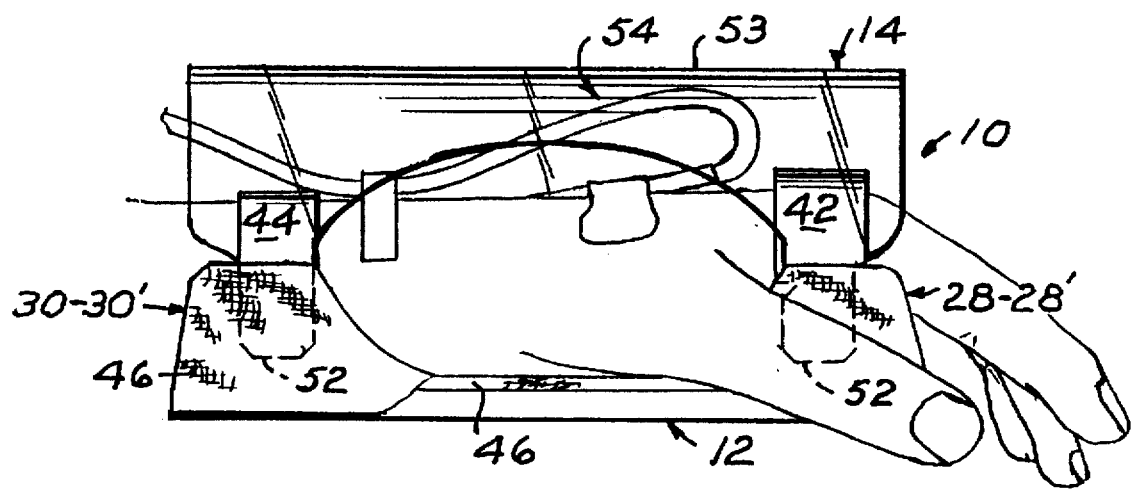
FIG. 1 is a side elevational view of the device illustrating the relative position of a patient's hand and fingers when secured thereto.

Like characters of reference designate like parts in those figures of the drawings in which they occur.

The reference numeral 10 indicates the device as a whole comprising a base 12 and an overlying transparent shield or cover 14.

Figure 4:
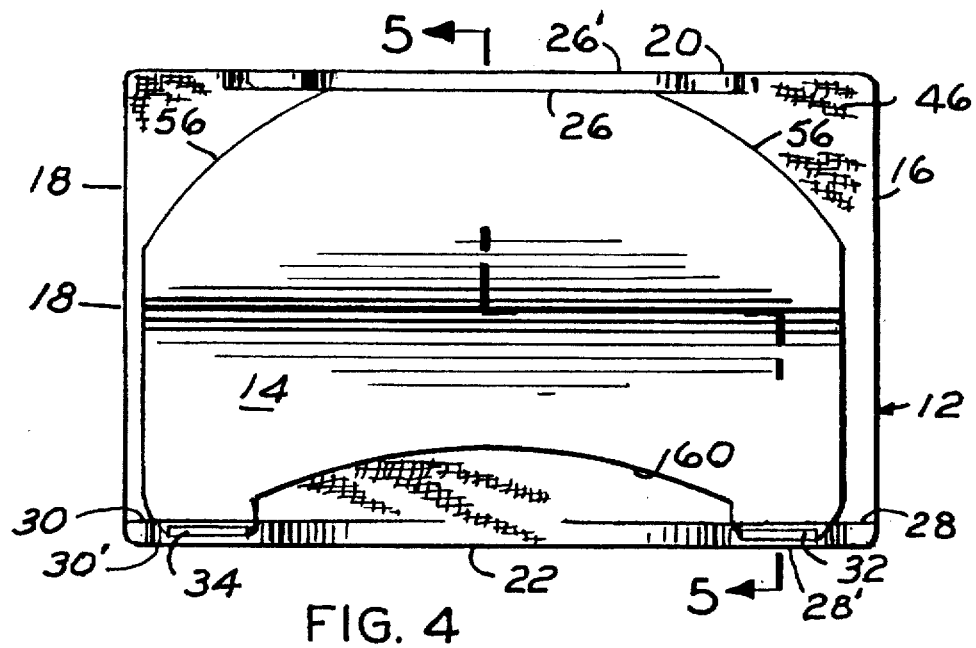
FIG. 4 is a top view.

The base 12 is formed by molded plastic and is characterized by a generally planar rectangular section having parallel forward and rearward end edges 16 and 18, respectively, and side edges 20 and 22 (FIG. 4). A wall extends upwardly from the base side edge 20 a distance not greater than one-half the width of the base planar portion and is turned downward by a return bend to form inner and outer walls 26 and 26' medially the ends of the base side 20 for the purposes presently explained.

The major central portion of the base is depressed downwardly a distance substantially equal with the thickness of the base material, as at 24 (FIG. 6), to form a base stiffener.

Figure 2:
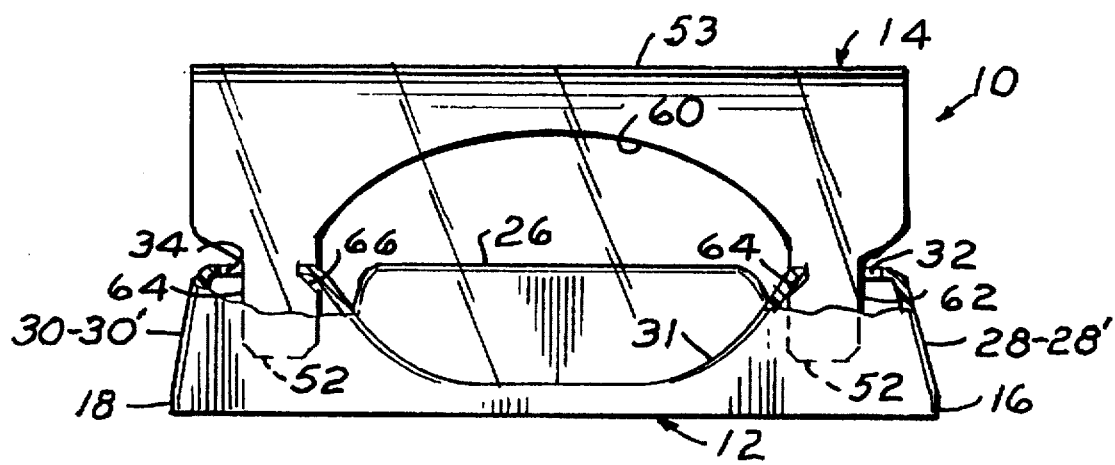
FIG. 2 is a side elevational view of the device, per se, having the cushion removed for clarity.
Figure 3:
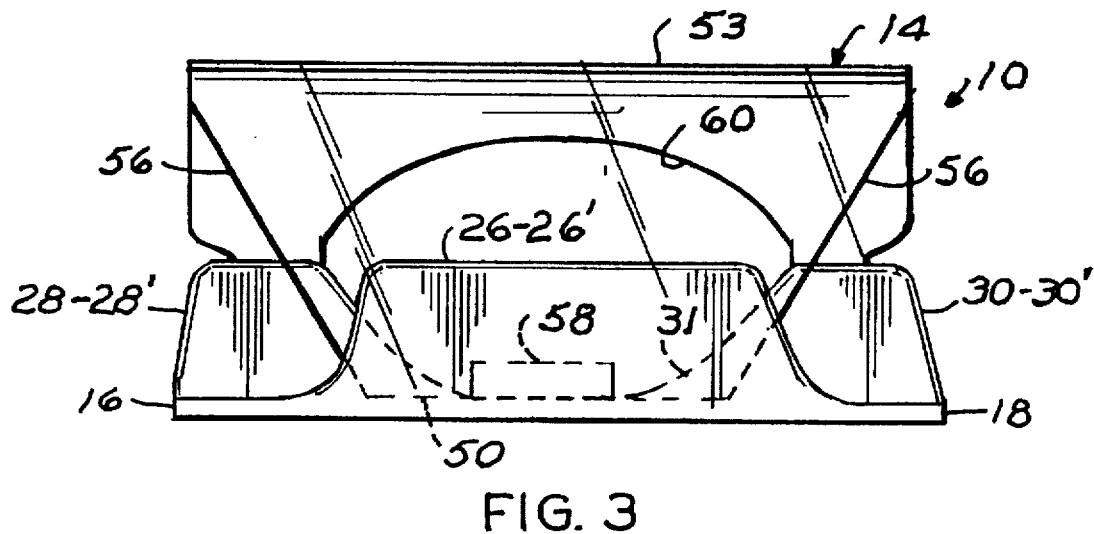
FIG. 3 is a side elevational view of the opposite side.

Similarly, at the opposite side of the base a wall extends upwardly at its forward and rearward end is and similarly turned downward by a return bend to form inner and outer walls, as at 28–28' and 30–30 . The return bend of the walls 28–28' and 30–30' are longitudinally apertured to form a slot-like in, as at 32 and 34 (FIG. 2), for the purposes presently explained.

The base side 22 and adjacent edges of the upstanding side walls 28–28' and 30–30' form an arcuate concave surface 31 extending upwardly, at respective ends, from the plane of the base top for receiving a patient's thumb when the hand is placed on the base 12 as illustrated by FIG. 1.

Adjacent its respective ends 16 and 18, the bottom surface of the base is provided with a pair of VELCRO strips 36 and 38 (FIG. 6) transversely secured to the base bottom surface between the respective end edge and the adjacent end portion of the base depressed section 24.

Figure 6:
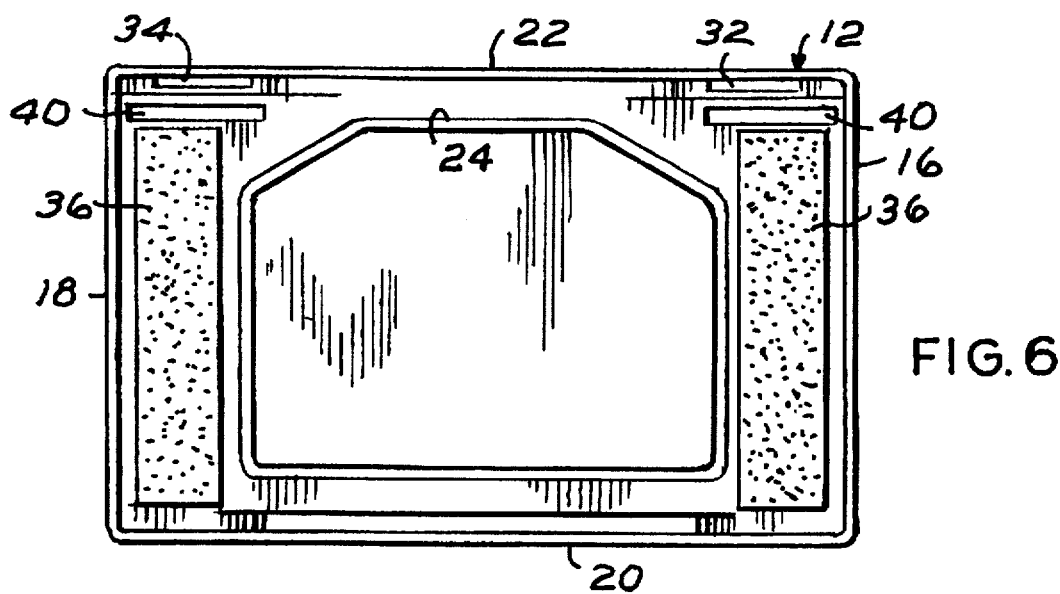

Spaced inwardly from the vertical plane of the inner side walls 28 and 30 the base is vertically slotted or apertured, as at 40 (FIG. 6), for receiving one end portion of a pair of straps 42 and 44 of hook and eye fabric material such as VELCRO secured to the respective VELCRO anchor strip 36 and 38 for extending around a patient's hand and wrist portion as illustrated by FIGS. 1 and 6.

A coextensive section of padding material 46, pleasing to the touch and having a nap cooperatively gripping VELCRO strap material when applied thereto overlies the base and outer surfaces of its respective side walls 26≧26', 28–28', and 30–30'.

The shield 14 is formed from a selected substantially rectangular section of transparent flexible plastic sheet material having a width substantially equal with the length of the base 12 and a dimension between its ends 50 and 52 so that, when manually arcuately bowed in an inverted U-shape form, its respective ends 50 and 52 are adjacent the upper limit of the base padding 46. The top of the shield bight portion 53 is spaced above the upper limit of a venipuncture site 54.

Figure 5:
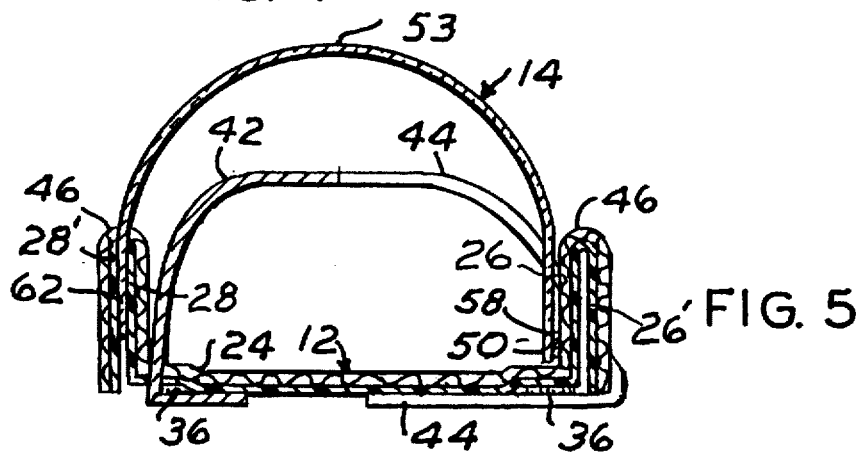
FIG. 5 is a vertical cross sectional view, including the cushion, taken substantially along the line 5—5 of FIG. 4; and, FIG. 6 is a bottom view.

The respective sides 56 of one shield end portion are preferably tapered toward its end and provided on its outer surface with a section of VELCRO material 58 for gripping and holding the shield end portion 50 adjacent the upper limit of the base when the VELCRO section 58 is pressed against the padding 46 overlying the inner surface of the side wall 26 (FIG. 5).

The other end portion of the shield is centrally arcuately recessed, as at 60, to define a pair of depending forward and rearward strips 62 and 64 having a width slightly less than the length of the slots 32 and 34 and a length less than the vertical height of the side walls 28–28' and 30–30'. Each of the strips 62 and 64 are provided with a substantially V-shaped notch 66 intermediate the ends of the confronting edge surfaces. The spacing between the strips is slightly less than the distance between the confronting ends of the slots 32 and 34. The strips 62 and 64 must be resiliently sprung apart manually when inserting or removing them from the slots 32 and 34. The notches 66 engage the respective end surface defining the adjacent ends of the slots 32 and 34 which prevents unauthorized removal of the strips from the slots.

Operation

The base, constructed as described hereinabove and provided with the overlying fabric padding 46 including the VELCRO straps 42 and 44, is attached to a patient's hand by placing the hand palm down on the base with the thumb projecting through the recess 31 and the fingers overlying the adjacent end surface. The VELCRO straps 42 and 44 are extended around the finger end of the hand and wrist portion and base to secure the base to the patient's hand. This may be done before inserting the catheter at the venipuncture site or following attaching the base to the patient's hand.

The strips 62 and 64 of the shield are first attached to the respective side walls 28 and 30 by inserting the strips 62 and 64 into the slots 32 and 34.

The shield opposite end portion 50 is then manually inserted between the double wall 26 and the patient's hand, opposite the thumb, and the fabric 46 overlying the wall 26, allowing the VELCRO section 58 to secure the end 50 portion to the fabric 46.

When it is desired to remove the shield for any purpose, one of the strips 62 or 64 is released from the wall slots by manually forcing one of the strip V-shape notch 66 out of contact with the end of the slot-like and similarly releasing the other strip notch 66 from the other slot so that the two strips may simultaneously be removed from the slots.

Trial and error practice has shown that this is much easier than attempting to remove the VELCRO padding securing the other end portion 50 of the shield to the padding.

Obviously the invention is susceptible to changes or alterations without defeating its practicability. Therefore, I do not wish to be confined to the preferred embodiment shown in the drawings and described herein.

I claim:

1. A shield for protecting the position of an intravenous needle having one end of intravenous tubing connected thereto when the needle is inserted into a body part of a patient, comprising:

a generally rectangular planar base having top, bottom, side and end surfaces and having pairs of longitudinally spaced upstanding inner and outer walls joined at their upper limit for defining an arcuate patient thumb receiving recess at one side of the base, the other side of said base having upstanding inner and outer walls joined at their upper limit medially the base ends, the upper limit of each pair of said pairs of forward and rearward side walls having a longitudinally extending wall slot, said base having a longitudinally extending slot adjacent its juncture with the respective pair of said pairs of side walls;

a first strip of fabric material transversely bonded to the bottom surface of said base adjacent its respective ends;

a plurality of flexible strap means respectively extending transversely of the base and through the base slots for securing a hand of a patient to the base;

an elongated inverted substantially U-shaped flexible transparent shield overlying said base and having opposite side edges and a bight portion and having leg portions depending from respective sides of the bight portion;

a recess in one said leg portion spaced inwardly from said side edges for defining a pair of substantially parallel shield strips removably received by the respective wall slot in each pair of said pairs of side walls;

each strip of said pair of strips having a notch in one side edge intermediate its ends for nesting the wall surface defining one end of the respective wall slot in each pair of said pairs of side walls; and, a second strip of fabric material secured to the other leg portion for cooperatively gripping said first fabric strip.

* * * * *